United States Patent [19]

Almen et al.

[11] Patent Number: 5,447,711

[45] Date of Patent: Sep. 5, 1995

[54] CONTRAST MEDIA

[75] Inventors: Torsten Almen; Lars Bååth, both of Malmö, both of Sweden; Audun N. Øksendal, Oslo, Norway

[73] Assignee: Nycomed Imaging AS, Oslo, Norway

[21] Appl. No.: 213,454

[22] Filed: Mar. 14, 1994

Related U.S. Application Data

[63] Continuation of Ser. No. 836,303, filed as PCT/EP90/01481, Sept. 1, 1990, abandoned.

[30] Foreign Application Priority Data

Sep. 4, 1989 [GB] United Kingdom ............... 8919929

[51] Int. Cl.⁶ ............................................. A61K 49/04
[52] U.S. Cl. ........................... 424/9.452; 424/9.453; 424/9.454
[58] Field of Search ................................. 424/5

[56] References Cited

U.S. PATENT DOCUMENTS

| 4,001,323 | 1/1977 | Felder et al. | 424/5 |
|---|---|---|---|
| 4,014,986 | 3/1977 | Tilly et al. | 424/5 |
| 4,250,113 | 2/1981 | Nordal et al. | 424/5 |
| 4,285,928 | 8/1981 | Wada et al. | 424/5 |
| 4,341,756 | 7/1982 | Sovak et al. | 424/5 |
| 4,396,598 | 8/1983 | Lin | 424/5 |
| 4,589,412 | 5/1986 | Kensey | 606/159 |
| 4,865,836 | 9/1989 | Long, Jr. | 424/5 |

FOREIGN PATENT DOCUMENTS

| 881234 | 5/1980 | Belgium . |
| 108638 | 5/1984 | European Pat. Off. . |
| 231091 | 8/1987 | European Pat. Off. . |
| 2041221 | 9/1980 | United Kingdom . |

OTHER PUBLICATIONS

Oda et al., Neurological Surgery, vol. 12, No. 12, pp. 1369–1377 (1984). (English Translation).
Oda et al., *Biol. Abstr.* 79(9):74398 (1985).
Lowe, *Chem Abstr.* 107:168089m (1987).
Tragarth et al., *Investigative Radiology*, 10, 3, 1975, 231–238.
Ralston et al., *Investigative Radiology*, 23, 1988, S140–S143.
Zucker et al., *Investigative Radiology*, 23, 1988, S340–S345.
Messana et al., *J. Pharmacol. Exp. Ther.*, 244, 3, 1987, 1139–1144.
Kim et al., *Biological Abstracts*, 90:70817, 1990.

*Primary Examiner*—Gary E. Hollinden
*Assistant Examiner*—Scott C. Rand
*Attorney, Agent, or Firm*—Bacon & Thomas

[57] ABSTRACT

The decrease in cardiac contractile force which occurs in angiography using contrast media may be reduced without increasing the incidence of ventricular fibrillations by oxygenating the contrast media.

10 Claims, 3 Drawing Sheets

Iohexol: ———●
Ioxaglate: ---------○

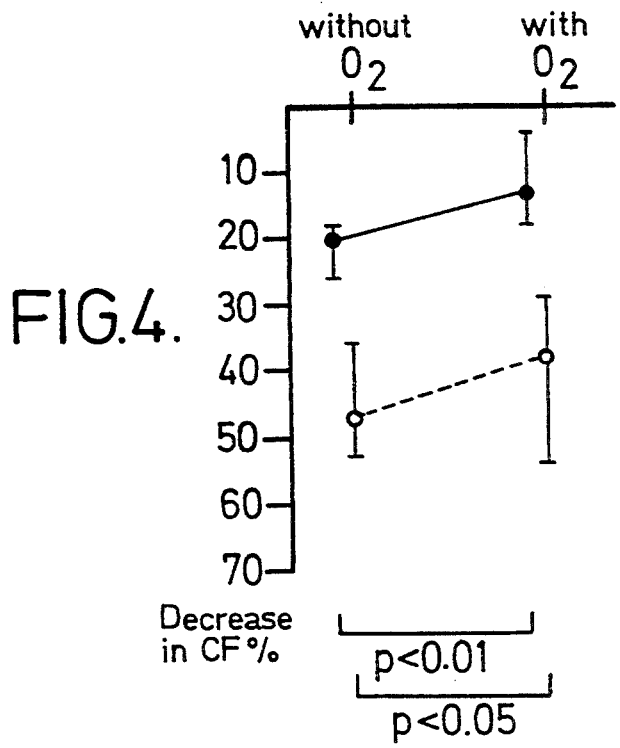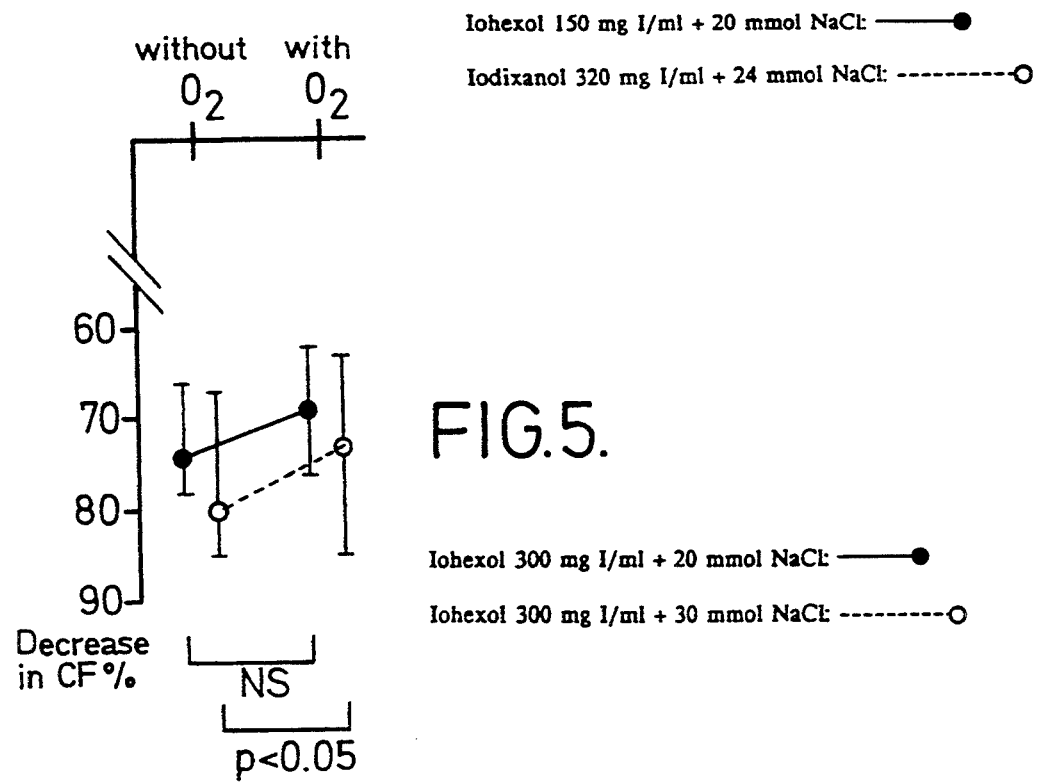

CONTRAST MEDIA

This application is a Continuation of application Ser. No. 07/836,303, filed as PCT/EP90/01481, Sept. 1, 1990 now abandoned.

This invention relates to contrast media, in particular X-ray contrast media and especially so-called non-ionic contrast media.

Contrast media generally fall into two groups, the so-called ionic and non-ionic contrast media. In these the contrast agent, in a carrier fluid, is respectively in ionic form or in molecular or particulate form.

Contrast media may be administered in medical imaging procedures, for example X-ray, magnetic resonance and ultrasound imaging, to enhance the image contrast in images of a subject, generally a human or non-human animal body. The resulting enhanced contrast enables different organs, tissue types of body compartments to be more clearly observed or identified. In X-ray imaging the contrast media function by modifying the X-ray absorption characteristics of the body sites into which they distribute; magnetic resonance contrast media generally function by modifying the characteristic relaxation times $T_1$ and $T_2$ of the nuclei, generally water protons, from the resonance signals of which the images are generated; and ultrasound contrast media function by modifying the speed of sound or the density in the body sites into which they distribute.

Clearly however the utility of a material as a contrast medium is governed to a large extent by its toxicity and any other adverse effects it may have on the subject to which it is administered. Since such media are conventionally used for diagnostic purposes rather than to achieve a direct therapeutic effect, when developing new contrast media there is a general desire to develop media having as little as possible an effect on the various biological mechanisms of the cells or the body as this will generally lead to lower animal toxicity and lower adverse clinical effects.

The toxicity and adverse effects of a contrast medium are contributed to by the components of the medium, e.g. the solvent or carrier as well as the contrast agent and its components (e.g. ions where it is ionic) and metabolites.

The following major contributing factors to contrast media toxicity and adverse effects have been identified:
 the chemotoxicity of the contrast agent,
 the osmolality of the contrast medium, and
 the ionic composition (or lack thereof) of the contrast medium.

Thus in coronary angiography, for example, injection into the circulatory system of contrast media has been associated with several serious effects on cardiac function, effects sufficiently severe as to place limitations on the use in angiography of certain contrast media.

In this procedure, for a short period of time a bolus of contrast medium rather than blood flows through the circulatory system and differences in the chemical and physicochemical nature of the contrast medium and the blood that it temporarily replaces can give rise to undesirable effects, e.g. arrhythmias, QT-prolongation, and, especially, reduction in cardiac contractile force and occurrence of ventricular fibrillation. There have been many investigations into these negative effects on cardiac function of infusion of contrast media into the circulatory system, e.g. during angiography, and means for reducing or eliminating these effects have been widely sought.

Thus for example Trägardh et al. (see Investigative Radiology 10:231–238 (1975)) found that the effects on cardiac function could be reduced if calcium ions were added to the contrast medium and in International Patent Application No. PCT/EP90/00393 it is disclosed that decrease in cardiac contractile force and occurrence of ventricular fibrillation may be reduced by inclusion of sodium ions in the contrast medium at 20–40 mM Na/liter, i.e. well below the normal plasma concentration.

Trägardh et al. also investigated the effect on the contractile force (CF) reduction which occurs on infusion of contrast media into the circulatory system of oxygenating the contrast medium but from their results concluded that oxygenation did not decrease the negative effects of the contrast medium on cardiac function and thus their results and conclusion clearly pointed away from oxygenation being a method of improving the biotolerability of contrast media.

BRIEF DESCRIPTION OF DRAWINGS

FIG. 4 shows the contractile force after infusing with iohexol-containing media or iodixanol, with sodium.

FIG. 5 shows the contractile force after infusing with sodium containing iohexol-containing contrast media with or without oxygenation.

Figure 1:
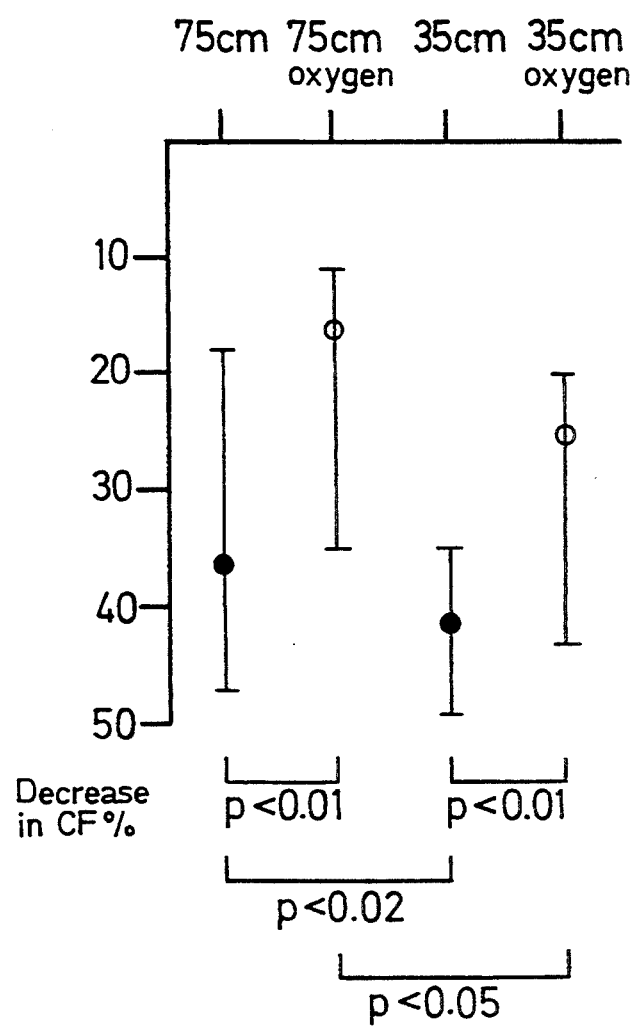
FIG. 1 shows the contractile force after infusing contrast media with or without oxygenation.

We have however now surprisingly found that adverse effects of contrast media can be reduced by oxygenation of the media.

The present invention lies in the surprising finding that oxygenation results in a decrease in the contractile force reducing effect of a contrast medium. This is coupled with the finding that the risk of ventricular fibrillation is not increased by oxygenation.

Thus, in one aspect, the invention provides a contrast medium comprising a contrast agent, preferably an iodinated X-ray contrast agent and especially preferably a non-ionic contrast agent, in a physiologically tolerable aqueous liquid carrier medium, characterised in that said contrast medium is oxygenated and with the provisos that said contrast medium comprises a said contrast agent other than metrizamide and that where said contrast agent is an ionic contrast agent it has a ratio of at least 3.

In the foregoing paragraph a reference is made to the non-ionic contrast agent metrizamide; this reference is made in view of the disclosure by Trägardh et al. supra of a metrizamide-containing contrast medium saturated with an oxygen/carbon dioxide mixture. Trägardh et al's investigations, however, disclosed no beneficial effects of oxygenation.

The contrast media of the invention may be oxygenated in any convenient fashion, e.g. by passage of oxygen or an oxygen-containing gas mixture through the medium e.g. for 5 minutes or more.

The oxygenated medium may then be filled into and sealed in a pharmaceutical container, most preferably with an oxygen or oxygen-containing headspace in the sealed container. In an alternative and simplified process variant, oxygenation of the contrast media may be effected after the medium is filled into and sealed in a pharmaceutical container, e.g. an ampoule, vial, flask or bottle. Thus it has been found that, where the headspace of the sealed container is oxygen or an oxygen-containing (preferably oxygen rich) gas, autoclaving the sealed containers serves to oxygenate the medium.

In a further aspect the invention also provides a process for the preparation of a contrast medium according to the invention, said process comprising oxygenating a composition comprising a physiologically tolerable aqueous liquid carrier medium and at least one non-ionic contrast agent other than metrizamide or an ionic contrast agent of at least ratio 3.

The use of pure oxygen may generally be preferred. However oxygenation can conveniently be effected using a gas mixture containing oxygen and carbon dioxide with a carbon dioxide content of 4% or less, especially 2% or less, (by partial pressure). The oxygen tension of the medium (which can for example be measured using a blood gas analyser (e.g. an ABL 330 pH/blood gas analyser from Radiometer of Copenhagen, Denmark)) is raised by oxygenation, conveniently to at least 30 kPa, preferably at least 40 kPa, particularly preferably at least 50 kPa, especially preferably at least 60 kPa and more especially at least 70 kPa. Oxygen tensions of 70 to 85 kPa or even up to levels as high as 115 or 120 kPa are particularly advantageous.

It will of course be particularly convenient simply to saturate the contrast medium with oxygen (using pure oxygen or an oxygen containing gas) at or near ambient pressure and body temperature or alternatively during a post-sealing thermal treatment, for example as described above.

The oxygenated contrast media of the invention are of course preferably stored in gas-tight containers. For this purpose conventional glass pharmaceutical bottles sealed with conventional rubber stoppers (e.g. PH701/45C available from Pharma-gummi) have been found to be adequate.

In the contrast media of the invention, the carrier medium is preferably a conventional aqueous medium.

The present invention is especially applicable to X-ray contrast media, in particular non-ionic contrast media and especially media containing contrast agents of ratio 3 or above, such as those mentioned below, especially iohexol, ioversol, iopamidol, iotrolan, ioxaglate and, particularly, iodixanol. (See GB-A-1548594, EP-A-83964, BE-A-836355, EP-A-33426, and EP-A-108638).

Other nonionic X-ray contrast agents which may be oxygenated according to the invention include: metrizamide (see DE-A-2031724), iodecimol (see EP-A-49745), ioglucol (see U.S. Pat. No. 4,314,055), ioglucamide (see BE-A-846657), ioglunide (see DE-A-2456685), iogulamide (see BE-A-882309), iomeprol (see EP-A-26281), iopentol (see EP-A-105752, iopromide (see DE-A-2909439), iosarcol (see DE-A-3407473), iosimide (see DE-A-3001292), iotasul (see EP-A-22056), and ioxilan (see WO-A-87/00757).

Most conventional X-ray contrast media contain as the contrast agent an iodine containing material. (Iodine which has a relatively high atomic weight accordingly has a relatively large cross-section to X-rays).

Thus the contrast medium used in angiography may have an iodine concentration as high as 250–450 mg I/ml and at that concentration range ionic contrast agents of ratio 1.5 (such as diatrizoate, iothalamate, ioxithalamate, iodamide and metrizoate) have an osmolality 5 to 9 times that of normal human plasma, ionic contrast agents of ratio 3 (e.g. ioxaglate) or non-ionic contrast agents of ratio 3 (e.g. metrizamide, iopromide, iopentol, iopamidol and iohexol) have an osmolality about a half as large, and non-ionic contrast agents of ratio 6 (e.g. iotrolan and iodixanol) have an osmolality about quarter that of the ratio 1.5 ionic contrast agents at the same iodine concentration. Ratio 6 non-ionic contrast agents may even be used at iodine concentrations where they are hypotonic so that normal plasma ions may be added to produce isotonicity with normal plasma.

By "ratio 3" in the above paragraph it is meant that the ratio of iodine atoms to contrast agent particles (i.e. ions or molecules) is 3. Ratio 1.5 and 3 ionic and ratio 3 and 6 non-ionic contrast agents generally contain one or two triiodophenyl moieties respectively.

Thus, for the most part, at iodine concentrations of for example 250 mg I/ml, X-ray contrast media will be hypertonic. This hypertonicity causes osmotic effects such as the draining out of water from red-blood cells, endothelial cells, and heart and blood vessel muscle cells. Loss of water makes red blood cells stiff and hypertonicity, chemotoxicity and non-optimal ionic make-up separately or together reduce the contractile force of the muscle cells and cause dilation of small blood vessels and a resultant decrease in blood pressure.

The contrast media of the invention, where they contain iodinated contrast agents, will particularly preferably contain such agents as concentrations of at least 100 mgI/ml. Moreover, while the general constraint that the deviation from isotonicity should if possible be minimized applies, it is generally preferable that the osmolality of the contrast media of the invention be less than 1 osm/kg $H_2O$, especially preferably 850 mosm/kg $H_2O$ or less.

As mentioned above, International Patent Application No. PCT/EP90/00393 describes how negative effects of contrast media on cardiac function may be diminished by the addition of sodium ions to the contrast medium to give a sodium concentration of from at least 20 up to 60 mM Na/liter.

We have now found that the inclusion of sodium ions, especially at concentrations of 20–30 mM Na/liter, together with oxygenation of the contrast medium results in particularly beneficial lowering of the decrease in CF.

Sodium ions may conveniently be incorporated within the contrast media of the invention in the form of sodium salts with physiologically tolerable counterions. Particularly suitable counterions include plasma anions such as chloride, phosphate and hydrogen carbonate ions. However, sodium may alternatively be incorporated, at least in part, in the form of a salt of a physiologically tolerable chelating agent, e.g. sodium edetate or calcium disodium edetate (for example to contribute 0.5 to 1.5 mM Na/liter to the overall sodium ion concentration). Besides sodium ions, other physiologically tolerable cations may be incorporated within the contrast media of the invention, e.g. calcium, potassium and magnesium ions. The contrast media of the invention may therefore conveniently be produced by the addition to existing contrast media of sodium salts, either as solids or already in solution, or of sodium-containing salt mixtures or solutions thereof, and oxygenation of the resulting media.

Moreover if desired the contrast media of the invention may also contain a buffer, e.g. one capable of maintaining the pH of the medium at 6.6 to 7.5.

According to another aspect of the present invention there is provided a method of imaging a human or non-human (preferably mammalian) animal body, which method comprises introducing an oxygenated contrast medium into the circulatory system of said body and generating an image of at least part of said body with the proviso that said contrast medium contains at least one non-ionic contrast agent other than metrizamide or an ionic contrast agent of at least ratio 3.

The present invention will now be described further with reference to the following investigations and non-limiting Examples:

INVESTIGATION OF THE EFFECT ON CARDIAC CONTRACTILE FORCE OF OXYGEN SATURATION OF CONTRAST MEDIA

Rabbit hearts were donated by rabbits of both sexes which were anaesthetized intravenously with pentobarbitone (Mebumal Vet, ACO) and heparinized (Heparin, KabiVitrum, 1000 IU/kg). The heart, lungs and aorta were quickly removed and placed in a bowl containing, at 4° C., Krebs' solution modified by addition of glucose 11.0 mmol/1 and sucrose 12.0 mmol/1. After removal of the lungs and mediastinal tissue the ascending aorta was mounted on a metal cannula (internal diameter/-outer diameter 1.6/2.0 mm) according to the Langendorff technique. The modified Krebs' solution, saturated with 95% (by partial pressure) oxygen and 5% carbon dioxide, was used for perfusion of the heart. The perfusion system was temperature controlled at 37° C. When the coronary perfusion had started, the pulmonary artery was incised to permit optimal drainage and to permit samples to be taken for oxygen tension measurements.

The perfusion fluid of Krebs' solution was oxygenated (with 95% oxygen and 5% carbon dioxide) and stored in a glass container. From the container the perfusion fluid was delivered through two parallel plastic tubes connected with a T-valve to the aortic catheter just above its entrance into the ascending aorta. The T-valve was turned so that the connection between one of the plastic tubes and the aortic catheter was closed. Contrast medium was then injected into the closed tube while perfusion fluid was simultaneously flowing through the other tube. Then the T-valve was turned so that the flow of perfusion fluid to the aortic catheter was stopped and the flow of contrast medium was started. If ventricular fibrillation (VF) occurred, the T-valve made it possible to stop the fibrillation by exchanging the flow of test solution for perfusion fluid. The heart preparation was therefore presumed protected from damage due to prolonged fibrillation. This also meant that, if VF occurred, the whole volume of contrast medium did not perfuse the heart.

After the heart was mounted, it was allowed to rest for 20 minutes with a perfusion pressure of 75 cm $H_2O$. A strain gauge (Dept of Medical Technology, Malmö General Hospital) was sutured to the wall of the left ventricle for measurement of the contractile force (CF) of the myocardium. The myocardium was slightly stretched between the two sutures. Needle electrodes for electrocardiography (ECG) were placed into the remnants of the mediastinal tissue behind the heart. A Mingograph 800 (Elema Schönander) was used for recordings of CF and ECG.

Low perfusion pressure (to imitate the effect of coronary arteriosclerosis) was created by raising the mounted rabbit heart until a perfusion pressure of 35 cm $H_2O$ was reached. The heart was perfused at low pressure for 5 minutes before the contrast medium was infused. After the contrast medium solution had passed the heart, or after VF had occurred, the heart was lowered to the normal perfusion pressure of 75 cm $H_2O$. If the next contrast medium infusion was to be performed at a perfusion pressure of 75 cm $H_2O$, the heart was then allowed to rest for 10 minutes. If the next contrast medium infusion was to be performed at a low perfusion pressure, the heart was allowed to rest for 7 minutes at a pressure of 75 cm $H_2O$ before again raising the heart to the pressure of 35 cm $H_2O$. The heart was then perfused at low pressure for 5 minutes before the contrast media were infused. The contrast media were infused into the heart at 37° C.

During normal perfusion pressure the median flow rate of Krebs' solution through the heart was 29 ml/min. During reduced perfusion pressure the median flow rate of Krebs' solution was 15 ml/min.

Oxygenation was performed by filling the desired amount of contrast medium into an empty 50 ml bottle with a thin bottle neck and perfusing the media with 100 percent oxygen. The oxygen was bubbled through a 3 mm wide plastic tube, which was perforated in its distal end. The tube was placed in the bottom of the bottle and 0.5 liter of oxygen per minute was bubbled through the solution for 5 minutes at 37° C. immediately before infusion into the heart. Samples for measurement of oxygen tension were taken from the contrast media before and after oxygen saturation. Samples were also taken from the nutrition fluid in the container, immediately before the fluid's entrance into the heart and, after having passed through the heart, from the incision in the pulmonary artery. An ABL 330 pH/blood gas analyzer (Radiometer, Copenhagen, Denmark) was used for measurements of oxygen tension.

In the container for the Krebs' solution, the oxygen tension was 80–85 kPa. Oxygen tension of the Krebs' solution immediately before its entrance into the heart was 73–80 kPa and after having passed through the heart 6.4–14.1 kPa. Oxygen tension of the contrast media before oxygen saturation was 23–24 kPa, after oxygen saturation 70–77 kPa.

The decrease in CF was measured as minimum contractile force during contrast medium infusion in percent of contractile force before infusion. The time period until reaching minimum contractile force was measured. When VF occurred, the time period from the beginning of the contrast medium infusion until the onset of VF was measured.

The following investigations were performed:

TEST 1

Sixteen rabbits were used (weight 2.3–2.8 kg). Iohexol (300 mg I/ml) was diluted with distilled water to reach an iodine concentration of 150 mg I/ml. Iohexol 150 mg I/ml was infused without or with oxygen saturation and during normal or reduced perfusion pressure, i.e. four infusions into each heart. The contrast media were infused in doses of 7.5 ml in random order.

TEST 2

Sixteen rabbits were used (weight 2.3–3.1 kg). Iohexol (300 mg I/ml) was diluted with distilled water to reach an iodine concentration of 150 mg I/ml. Iohexol 150 mg I/ml was infused without sodium addition or with 28 mmol $Na^+/1$ added as solid NaCl. The contrast media were infused without or with oxygen saturation during reduced perfusion pressure (35 cm H₂O), i.e. four infusions into each heart. The contrast media were infused in doses of 7.5 ml in random order (N.b. Iohexol stock solution contains less than 1 mmol Na+/l).

TEST 3

Iohexol (Omnipaque 300 mg I/ml, Nycomed AS) was diluted with distilled water to reach an iodine concentration of 160 mg I/ml.

Ioxaglate 160 mg I/ml (Hexabrix, Laboratoire Guerbet) was also infused. The contrast media were infused with and without oxygen saturation and CF was measured. A volume of 10 ml of each of the four contrast media was infused into 10 rabbit hearts in random order, i.e. a total of 40 infusions. The weights of the rabbits were 2.7–3.5 kg.

TEST 4

Iohexol (300 mg I/ml) was diluted with a stock solution of NaCl to reach an iodine concentration of 150 mg I/ml and a sodium concentration of 20 mmol/l. Iodixanol 320 mg I/ml (Nycomed A/S) containing 24 mmol/l, NaCl was also infused. The two contrast media were infused with and without oxygen saturation and CF was measured. A volume of 7.5 ml of each of the four contrast media was infused into 15 rabbit hearts in random order, i.e. a total of 60 infusions. The weights of the rabbits were 2.6–3.1 kg.

TEST 5

To iohexol (300 mg I/ml) 20 or 30 mmol Na+/l was added as solid NaCl. The contrast media were infused with and without oxygen saturation and CF was measured. A volume of 10 ml of each of the four contrast media was infused into 15 rabbit hearts in random order, i.e. a total of 60 infusions. The weights of the rabbits were 2.5–3.2 kg.

TEST 6

To iohexol (350 mg I/ml) no sodium or 10 mmol Na+/l as solid NaCl were added. The contrast media were infused with and without oxygen saturation. The frequency of ventricular fibrillations or other major arrhythmias was measured. A volume of 7.5 ml of each of the four contrast media was infused into 10 rabbit hearts, i.e. a total of 40 infusions. The weights of the rabbits were 2.4–3.4 kg.

Wilcoxon signed rank test was used for statistical analyses of contractile force and the time to reach minimum CF or time to reach VF. The fourfold table test with Yate's correction was used for statistical analysis of CF. A p-value $\leq 0.05$ was considered significant.

RESULTS

All contrast media infusions caused a median decrease in CF.

TEST 1

The contractile force (median decrease and interquartile range) after infusing contrast media with or without oxygenation and during normal (75 cm H₂O) or reduced (35 cm H₂O) perfusion pressure, is shown in FIG. 1 of the accompanying drawings. With both normal and reduced perfusion pressure, oxygenation caused a significantly smaller decrease in CF compared to no oxygenation ($p \leq 0.01$). With normal perfusion pressure, the oxygenation caused an improvement in CF from −37 percent to −16.5 percent; during reduced perfusion pressure, oxygenation caused an improvement in CF from −42 percent to −25.5 percent.

The median decrease in CF when infusing iohexol containing media without oxygenation was significantly smaller at normal perfusion pressure than at reduced perfusion pressure ($p \leq 0.02$). The median decrease in CF when infusing oxygenated iohexol-containing contrast media was significantly smaller at normal perfusion pressure than at reduced perfusion pressure ($p \leq 0.05$).

TEST 2

Figure 2:
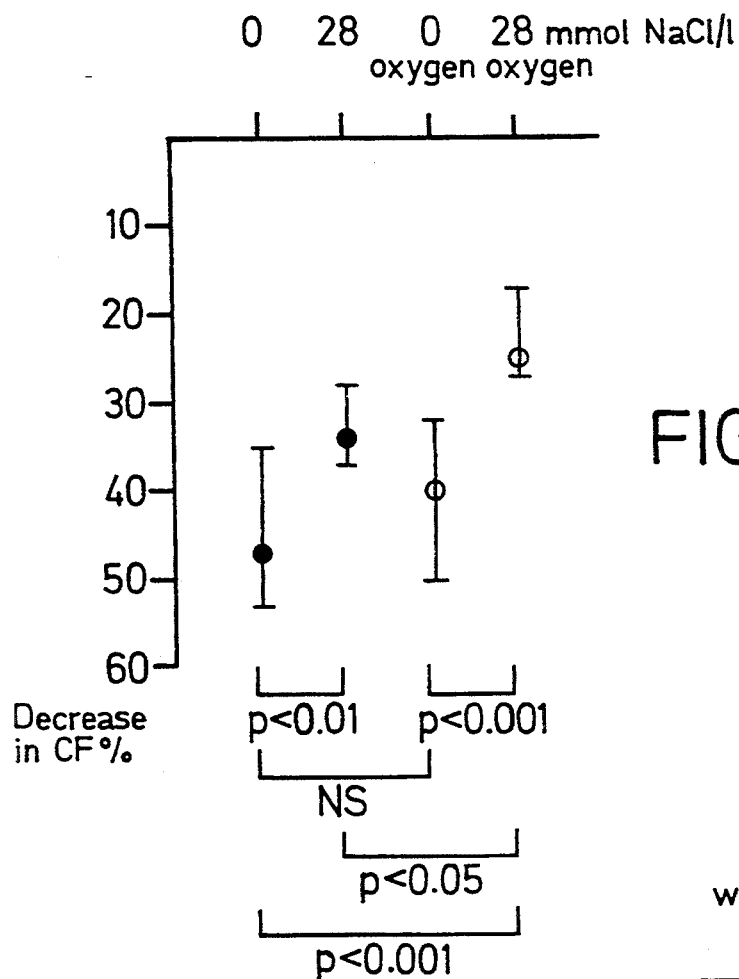
FIG. 2 shows the contractile force after infusing contrast media with or without sodium.

The contractile force (median decrease and interquartile range) after infusing contrast media with or without sodium addition of 28 mmol/l NaCl is shown in FIG. 2 of the accompanying drawings. All contrast media were infused at reduced (35 cm H₂O) perfusion pressure. When infusing media without sodium, and without oxygenation, the decrease in CF was 47 percent, whereas with oxygenation the decrease was 40 per cent. When infusing media with 28 mmol NaCl, oxygenation caused a significantly smaller decrease in CF (−25%) compared to that observed with non-oxygenated sodium containing media (−35%) ($p \leq 0.05$).

The median decrease in CF when infusing non-oxygenated iohexol containing contrast media was significantly smaller for media containing 28 mmol/l NaCl than for such contrast media without sodium addition ($p \leq 0.01$). The median decrease in CF when infusing oxygenated iohexol containing media was significantly smaller for media with 28 mmol/l NaCl than for media without sodium addition ($p \leq 0.01$). In particular, oxygenated iohexol containing media with 28 mmol/l NaCl caused a decrease in CF of 25 percent which was significantly less than the 47% decrease for non-oxygenated iohexol containing media to which no NaCl was added ($p \leq 0.001$).

TEST 3

Figure 3:
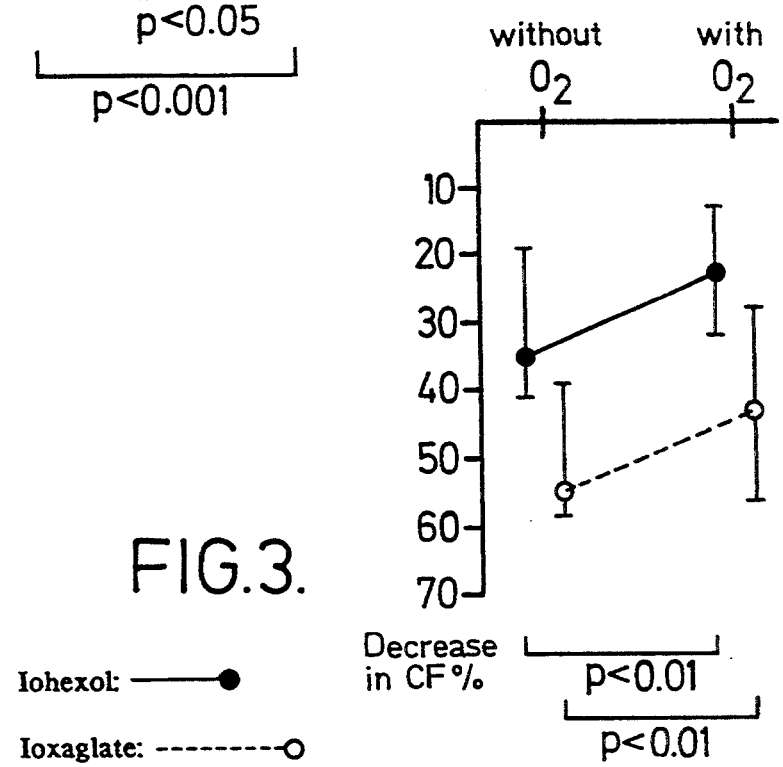
FIG. 3 shows the contractile force after infusing with iohexol or ioxaglate-containing contrast media.

The contractile force (median decrease and interquartile range) after infusing with iohexol or ioxaglate-containing contrast media with and without oxygenation is shown in FIG. 3 of the accompanying drawings. Oxygenation of iohexol containing media caused an improvement in CF reduction from −35% to −23% ($p \leq 0.01$). Oxygenation of ioxaglate containing media caused an improvement in CF reduction from −54.5% to −43% ($p \leq 0.01$).

TEST 4

The contractile force (median decrease and interquartile range) after infusing with iohexol-containing media or iodixanol with and without oxygenation are shown in FIG. 4 of the accompanying drawings. The contrast media contained 20–24 mmol/l NaCl. Oxygenation of 150 mg I/ml iohexol containing media caused an improvement in CF reduction from −20 percent to −13 percent ($p \leq 0.01$). Oxygenation of iodixanol containing media caused an improvement in CF reduction from −47 percent to −38 percent ($p \leq 0.05$).

The improvement in CF reduction from oxygenation was significantly larger for iodixanol than for iohexol.

TEST 5

The contractile force (median decrease and interquartile range) after infusing with iohexol containing contrast media with and without oxygenation are shown in FIG. 5 of the accompanying drawings. Contrast media with 20 or 30 mmol/l NaCl were used. Oxygenation of media with 30 mmol/l NaCl caused a significant improvement in CF reduction from −80 percent to −73 percent ($p \leq 0.05$). Oxygenation of media with 20 mmol/l NaCl caused a change in CF from −74 percent to 69 percent. When iohexol containing media with 20 mmol/l NaCl was infused in one of the hearts, severe arrhythmias made calculation of CF impossible. This occurred both with and without oxygenation of the contrast medium and the two infusions were not included in the calculated results.

When all infusions of oxygenated iohexol containing contrast media are compared to all infusions of non-oxygenated iohexol containing contrast media, a significant improvement in CF reduction is found for the oxygenated media. When all infusions of iohexol containing media are compared to all infusions of iohexol containing media with 30 mmol/l NaCl the smallest decrease in CF is caused by iohexol containing 20 mmol/l NaCl.

TEST 6

No significant difference in frequency of VF or multiple VES was found between media with or without oxygenation. Media without sodium caused a significantly higher frequency of VF and multiple VES than media with 10 mmol/l NaCl.

EXAMPLE 1

Oxygen was passed through a sterile 0.2 micrometer air filter and then bubbled through 5 liters of aqueous iohexol solution (OMNIPAQUE, 350 mgI/ml from Nycomed AS) at a flow rate of 5–6 liters/minute. The oxygenated solution was filled into 50 ml (32 mm) glass bottles, oxygen was added to the headspace and the bottles were sealed with PH701/45C rubber stoppers (from Pharma-gummi).

Iohexol 140, 300 and 350 mgI/ml with 28 mM/l NaCl added were similarly oxygenated and packaged.

EXAMPLE 2

Aqueous iohexol solution (OMNIPAQUE, 350 mgI/ml) was filled into 50 ml (32 mm) glass bottles, oxygen was added to the headspace and the bottles were sealed with PH701/45C rubber stoppers. The sealed bottles were then autoclaved at 121° C. (for $F_0 = 15$). The heating up/autoclaving period lasted about 30–40 minutes.

The oxygen content of the headspace and of the contrast medium was subsequently determined by gas chromatography and using a blood gas analyser (type ABL 330 from Radiometer) respectively. The values below are averages for three samples:
  Headspace oxygen : 95.7%
  Oxygen in contrast medium : 90.3 kPa OMNIPAQUE 140 and 300 mgI/ml solutions were treated and tested analogously yielding the following results:

| mgI/ml | Headspace oxygen | Oxygen in contrast medium |
|---|---|---|
| 140 | 93% | 109 kPa |
| 300 | 96% | 96 kPa |

We claim:

1. A physiologically tolerable composition consisting essentially of an oxygenated aqueous solution of an iodinated X-ray contrast agent, said solution having an oxygen tension of at least 60 kPa, wherein if said contrast agent is an ionic compound, it has an iodine ratio of at least 3 and wherein said contrast agent is other than metrizamide.

2. A composition as claimed in claim 1 containing a non-ionic X-ray contrast agent.

3. A composition as claimed in claim 1 containing a contrast agent selected from iohexol, ioversol, iopamidol, iotrolan, ioxaglate and iodixanol.

4. A composition as claimed in claim 1 having a pH in the range 6.6 to 7.5.

5. A composition as claimed in claim 1 having a sodium ion concentration of 20 to 60 mM.

6. A method of X-ray imaging a human or non-human animal body, which method comprises introducing by bolus injection an oxygenated contrast composition as claimed in claim 1 into said body and generating an X-ray image of at least part of said body containing said contrast agent.

7. A method of X-ray imaging a human or non-human animal body, which method comprises introducing by bolus injection an oxygenated contrast medium composition as claimed in claim 2 into said body and generating an X-ray image of at least part of said body containing said contrast agent.

8. A method of X-ray imaging a human or non-human animal body, which method comprises introducing by bolus injection an oxygenated contrast medium composition as claimed in claim 3 into said body and generating an X-ray image of at least part of said body containing said contrast agent.

9. A method of X-ray imaging a human or non-human animal body, which method comprises-introducing by bolus injection an oxygenated contrast medium composition as claimed in claim 4 into said body and generating an X-ray image of at least part of said body containing said contrast agent.

10. A method of X-ray imaging a human or non-human animal body, which method comprises introducing by bolus injection an oxygenated contrast medium composition as claimed in claim 5 into said body and generating an X-ray image of at least part of said body containing said contrast agent.

* * * * *